(12) United States Patent
Watakabe et al.

(10) Patent No.: US 9,008,406 B2
(45) Date of Patent: *Apr. 14, 2015

(54) METHOD AND APPARATUS FOR DISCRIMINATING UNDIFFERENTIATED PLURIPOTENT STEM CELLS, AND AUTOMATED CULTURE METHOD AND SYSTEM

(75) Inventors: Keizo Watakabe, Kobe (JP); Yohichi Nakamura, Kobe (JP); Osamu Ohji, Hyogo (JP); Katsumi Nakashima, Kobe (JP)

(73) Assignee: Kawasaki Jukogyo Kabushiki Kaisha, Kobe (JP)

( * ) Notice: Subject to any disclaimer, the term of this patent is extended or adjusted under 35 U.S.C. 154(b) by 327 days.

This patent is subject to a terminal disclaimer.

(21) Appl. No.: 13/500,626

(22) PCT Filed: Oct. 7, 2010

(86) PCT No.: PCT/JP2010/006007
§ 371 (c)(1),
(2), (4) Date: Jun. 26, 2012

(87) PCT Pub. No.: WO2011/043077
PCT Pub. Date: Apr. 14, 2011

(65) Prior Publication Data
US 2012/0315620 A1 Dec. 13, 2012

(30) Foreign Application Priority Data
Oct. 9, 2009 (JP) .................................. 2009-235306

(51) Int. Cl.
*G06K 9/00* (2006.01)
*G01N 33/50* (2006.01)

(52) U.S. Cl.
CPC .................................. *G01N 33/5073* (2013.01)

(58) Field of Classification Search
None
See application file for complete search history.

(56) References Cited

U.S. PATENT DOCUMENTS 7,711,174 B2 * 5/2010 Sammak et al. ............... 382/133
7,907,769 B2 * 3/2011 Sammak et al. ............... 382/133

(Continued)

FOREIGN PATENT DOCUMENTS

| EP | 2 143 791 A1 | 1/2010 |
| JP | 2002-223791 A | 8/2002 |

(Continued)

OTHER PUBLICATIONS

Computer generate english translation for JP 2006-042663 dated Feb. 2006.*

(Continued)

*Primary Examiner* — Nancy Bitar
(74) *Attorney, Agent, or Firm* — Marshall, Gerstein & Borun LLP

(57) ABSTRACT

Provided are a method capable of discriminating between a colony of differentiated pluripotent stem cells and a colony of undifferentiated pluripotent stem cells, and a method for automatically culturing undifferentiated pluripotent stem cells and a system thereof.

A differentiated colony composed of differentiated pluripotent stem cells, an undifferentiated colony composed of undifferentiated pluripotent stem cells and a multilayered colony having pluripotent stem cells stacked in multiple layers are discriminated by processing a photo image of a colony including pluripotent stem cells in a culture vessel. Specifically, a colony having a luminance higher than a first threshold A is determined as a differentiated colony, a colony having a luminance equal to or lower than the first threshold A and equal to or higher than a second threshold B is determined as an undifferentiated colony, and a colony having a luminance lower than the second threshold B is determined as a multilayered colony.

12 Claims, 17 Drawing Sheets

(56) References Cited

U.S. PATENT DOCUMENTS

| | | | |
|---|---|---|---|
| 7,920,736 B2* | 4/2011 | Sammak et al. | 382/133 |
| 7,993,864 B2* | 8/2011 | Brown et al. | 435/7.24 |
| 8,685,898 B2* | 4/2014 | Wiley | 506/26 |
| 2002/0086344 A1 | 7/2002 | Tsuji et al. | |
| 2003/0179916 A1 | 9/2003 | Magnuson et al. | |
| 2005/0176152 A1 | 8/2005 | Lopez et al. | |
| 2006/0039593 A1* | 2/2006 | Sammak et al. | 382/133 |
| 2007/0212778 A1* | 9/2007 | Bramke et al. | 435/326 |
| 2007/0243564 A1* | 10/2007 | Lawson et al. | 435/7.23 |
| 2007/0274963 A1* | 11/2007 | Green et al. | 424/93.7 |
| 2009/0029462 A1 | 1/2009 | Beardsley et al. | |
| 2010/0074507 A1* | 3/2010 | Klottrup et al. | 382/133 |
| 2011/0019897 A1* | 1/2011 | Takagi et al. | 382/133 |

FOREIGN PATENT DOCUMENTS

| | | | |
|---|---|---|---|
| JP | 2002-535027 A | | 10/2002 |
| JP | 2003-527106 A | | 9/2003 |
| JP | 2006-042663 A | | 2/2006 |
| JP | 2006042663 | * | 2/2006 |
| JP | 2007-024612 A | | 2/2007 |
| JP | 2007-522475 A | | 8/2007 |
| JP | 2009-022284 A | | 2/2009 |
| JP | 2009-044974 A | | 3/2009 |
| JP | 2009-077635 A | | 4/2009 |
| WO | WO-96/31522 A1 | | 10/1996 |
| WO | WO-00/42912 A1 | | 7/2000 |
| WO | WO-01/42786 A2 | | 6/2001 |
| WO | WO-01/51007 A2 | | 7/2001 |
| WO | WO-2008/117813 A1 | | 10/2008 |
| WO | WO-2009/006422 A1 | | 1/2009 |

OTHER PUBLICATIONS

Extended European Search Report for EP 11 797 850.2, dated Jan. 28, 2014.

Nakajima et al., "Saisei Iryo yo Saibo Baiyo no Jidoka Gijutsu," Biotechnology, 2007, vol. 85, No. 10, pp. 432-434.

International Search Report for PCT/JP2010/006007, mailed Dec. 7, 2010.

Inoue et al., "C-gengo de Manabu Jissen Gazo Shori," pp. 84-91, 1999.

Nakashima et al., "Development of the automatic cell processing machine for the adherent cell," Inflamm Regen., vol. 29, No. 2, pp. 131-134, 2009.

Nakashima et al., "Automation of Cell Culturing for Regeneration Medicine," Biotechnology, 2007, vol. 85, No. 10, pp. 432-434.

* cited by examiner

METHOD AND APPARATUS FOR DISCRIMINATING UNDIFFERENTIATED PLURIPOTENT STEM CELLS, AND AUTOMATED CULTURE METHOD AND SYSTEM

TECHNICAL FIELD

The present invention relates to a method and apparatus for discriminating undifferentiated pluripotent stem cells, and an automated culture method and system. More specifically, the present invention relates to a method and apparatus for discriminating between undifferentiated pluripotent stem cells and other pluripotent stem cells, and a method and system for automatically culturing the undifferentiated stem cells using the method and apparatus.

BACKGROUND ART

In recent years, pluripotent stem cells such as ES cells and iPS cells (herein, "ES cells" and "iPS cells" are collectively referred to as "pluripotent stem cells") have been artificially created and much contribution is expected in the field of regenerative medicine. Pluripotent stem cells have universal differentiability, i.e., being differentiable into various types of cells constituting a living body; therefore, the skin, cartilage, bone, blood vessel, nerve, or organs of a patient can be regenerated without causing rejection by using the patient's own iPS cells.

Since pluripotent stem cells have universal differentiability as described above, there may be cases in which apart of pluripotent stem cells may start differentiating during culturing. The cells which have started to differentiate cannot be reverted to an undifferentiated state and can no longer be used for creating internal organs and organum as aimed. Therefore, during the subculture of pluripotent stem cells, it is important to selectively subculture only undifferentiated pluripotent stem cells.

Such discrimination of the undifferentiated pluripotent stem cells can be carried out by observing cells after being stained or under fluorescent light, using, for example, "CellCelector" manufactured by "AVISO". However, cell staining is often performed on the cells after being fixed, in general, and dyes are often toxic to cells; therefore, it is difficult to observe the cells while they are still alive. Even the use of a dye with low toxicity is still harmful to the cells and unsuitable for the application in the field of regenerative medicine.

SUMMARY OF INVENTION

Technical Problem

The present invention was made to solve the foregoing problems in the conventional art and an object of the present invention is to provide a method and apparatus capable of selectively discriminating a colony composed only of undifferentiated pluripotent stem cells even in the case in which a portion of the pluripotent stem cells has started to differentiate during culturing, and to provide a method and system enabling automatic culturing of only undifferentiated stem cells.

Solution to Problem

A colony discrimination method according to an aspect of the present invention is a method for discriminating a colony based on a photo image of the colony composed of pluripotent stem cells in a culture vessel, and the method is characterized by discriminating between a differentiated colony containing differentiated pluripotent stem cells and an undifferentiated colony containing only undifferentiated pluripotent stem cells based on the luminance of the photo image.

Although "differentiated pluripotent stem cell" is regarded as being no longer "pluripotent", this term is used herein for the sake of convenience.

In another aspect of the aforementioned method, it is possible to configure that a multilayered colony containing pluripotent stem cells stacked in multiple layers can be additionally discriminated based on the luminance of the colony.

In the aforementioned method, it is possible to configure such that a colony having a region with a luminance higher than the first threshold of the luminance is determined as the differentiated colony and a colony having only a region with a luminance equal to or lower than the first threshold is determined as the undifferentiated colony.

Further, it is also possible to configure such that: a colony having a region with a luminance higher than the first threshold of the luminance is determined as the differentiated colony; a colony having only a region with a luminance equal to or lower than the first threshold and equal to or higher than a second threshold is determined as the undifferentiated colony; and a colony having a region with a luminance lower than the second threshold as the multilayered colony.

In other aspect of the method, the first threshold may be determined by applying a discriminant analysis to the distribution of the number of pixels with respect to each luminance value determined on a median filtered image obtained by applying median filtering once or multiple times to the photo image mentioned above.

Also, the second threshold may be determined as in the following. Specifically, the second threshold may be determined by: obtaining an image of only the colony region by extracting, out of the pixels in the smoothing filtered image obtained by applying smoothing filtering once or multiple times to the photo image, only the pixels having a luminance value equal to or smaller than the threshold calculated by multiplying the first threshold by a predetermined multiplying factor in the range of from 105% to 115%; creating a histogram with respect to each pixel in the image of only the colony region, with the luminance value on the horizontal axis and the number of pixels having the corresponding luminance value on the vertical axis; provided that a maximum luminance limit defined as whichever the smaller luminance value between the first threshold and the luminance value corresponding to the maximum value of the histogram, obtaining within the range of luminance value smaller than the maximum luminance limit, a straight line by the least squares method using the coordinates of the points on the histogram that lie between 20% of the number of pixels corresponding to the maximum luminance limit and 90% of the number of pixels corresponding to the maximum luminance limit; and obtaining the intersection point of the straight line and the horizontal axis.

A method for automatically culturing undifferentiated pluripotent stem cells according to another aspect of the present invention is characterized by including: a step for discriminating an undifferentiated colony from a colony other than the undifferentiated colony by any one of aspects of the discrimination method described above; a step for acquiring the positional information of the undifferentiated colony and that of the colony other than the undifferentiated colony; a step for introducing a cell detaching agent into the culture vessel; a step for detaching the undifferentiated colony based on the positional information; and a step for recovering the undifferentiated pluripotent stem cells obtained by detaching the undifferentiated colony.

Also, a method for automatically culturing undifferentiated pluripotent stem cells according to still another aspect of the present invention is characterized by including: a step for discriminating an undifferentiated colony from a colony other than the undifferentiated colony by the method for discriminating a colony according to any one of aspects described above; a step for acquiring the positional information of the undifferentiated colony and that of the colony other than the undifferentiated colony; a step for introducing a cell detaching agent into the culture vessel; a step for detaching the colony other than the undifferentiated colony based on the positional information; a step for discarding the pluripotent stem cells obtained by detaching the colony other than the undifferentiated colony; and a step for recovering the undifferentiated pluripotent stem cells by detaching the undifferentiated colony.

A colony discrimination apparatus according to still another aspect of the present invention is characterized by having an image input unit for inputting a photo image after subjected to image processing based on the luminance value, and a discrimination unit for discriminating between a differentiated colony containing differentiated pluripotent stem cells and an undifferentiated colony composed only of undifferentiated pluripotent stem cells.

In the apparatus according to other aspect, the discrimination unit can be configured so as to further discriminate a multilayered colony containing pluripotent stem cells stacked in multiple layers based on the luminance of the colony.

In the apparatus according to yet other aspect, the discrimination unit can be configured so as to determine: a colony having a region with a luminance higher than the first threshold of the luminance as the differentiated colony; and a colony having only a region with a luminance equal to or lower than the first threshold as the undifferentiated colony.

Further, the discrimination unit can be also configured so as to determine: a colony having a region with a luminance higher than the first threshold as the differentiated colony; a colony having only a region with a luminance equal to or lower than the first threshold and equal to or higher than a second threshold as the undifferentiated colony; and a colony having a region with a luminance lower than the second threshold as the multilayered colony.

In other aspect of the apparatus, the first threshold may be determined by applying a discriminant analysis to the distribution of the number of pixels with respect to each luminance value determined on a median filtered image obtained by applying median filtering once or multiple times to the photo image mentioned above.

Also, the second threshold may be determined as in the following. Specifically, the second threshold may be determined by: obtaining an image of only the colony region by extracting, out of the pixels in the smoothing filtered image obtained by applying smoothing filtering once or multiple times to the photo image, only the pixels having a luminance value equal to or smaller than the threshold calculated by multiplying the first threshold by a predetermined multiplying factor in the range of from 105% to 115%; creating a histogram with respect to each pixel in the image of only the colony region, with the luminance value on the horizontal axis and the number of pixels having the corresponding luminance value on the vertical axis; provided that a maximum luminance limit defined as whichever the smaller luminance value between the first threshold and the luminance value corresponding to the maximum value of the histogram, obtaining within the range of luminance value smaller than the maximum luminance limit, a straight line by the least squares method using the coordinates of the points on the histogram that lie between 20% of the number of pixels corresponding to the maximum luminance limit and 90% of the number of pixels corresponding to the maximum luminance limit; and obtaining the intersection point of the straight line and the horizontal axis.

The system for automatically culturing undifferentiated pluripotent stem cells according to another aspect of the present invention is characterized by having: the colony discrimination apparatus according to any one of the aspects described above; a detaching agent introduction unit for introducing a cell detaching agent into the culture vessel; and a pipetting unit for detaching the undifferentiated colony based on the positional information of each of the colony and recovering the undifferentiated pluripotent stem cells obtained by detaching the undifferentiated colony.

In addition, the system for automatically culturing undifferentiated pluripotent stem cells according to still another aspect of the present invention is characterized by having: the colony discrimination apparatus described above; a positional information acquisition unit for acquiring the positional information of the undifferentiated colony and that of the colony other than the undifferentiated colony; a detaching agent introduction unit for introducing a cell detaching agent into the culture vessel; and a pipetting unit for detaching the colony other than the undifferentiated colony based on the positional information acquired by the positional information acquisition unit, discarding the pluripotent stem cells obtained by detaching the colony other than the undifferentiated colony, and recovering undifferentiated pluripotent stem cells by further detaching the undifferentiated colony.

Advantageous Effects of Invention

The colony discrimination method and apparatus of the present invention enable discrimination between a differentiated colony and an undifferentiated colony based on the luminance of each colony by obtaining a photo image of colony composed of pluripotent stem cells in a culture vessel, and subjecting the same to image processing. Moreover, provided are an automated culture method and system capable of selectively subculturing only the undifferentiated pluripotent stem cells by thus discriminating the colony.

DESCRIPTION OF EMBODIMENTS

An embodiment of the present invention is explained below with reference to drawings, but the present invention is not limited to the following descriptions.

The discrimination method of the present invention discriminates between a differentiated colony containing differentiated pluripotent stem cells and an undifferentiated colony containing only undifferentiated pluripotent stem cells. Further, it can also discriminate a multilayered colony containing pluripotent stem cells stacked in multiple layers. After an image of pluripotent stem cells constituting a colony cultured in a culture vessel is subjected to image processing, the discrimination is carried out based on the luminance of each colony in the processed image. The image processing in this method mainly means normalizing the luminance of each pixel to, for example, a luminance falling within the range of gray scale intensity levels of from 0 to 255 (8 bits). Although this embodiment of the present invention uses 8 bit, 256 intensity levels, the present invention is not limited thereto, and it is possible to set the intensity levels to be larger or smaller.

Figure 1:
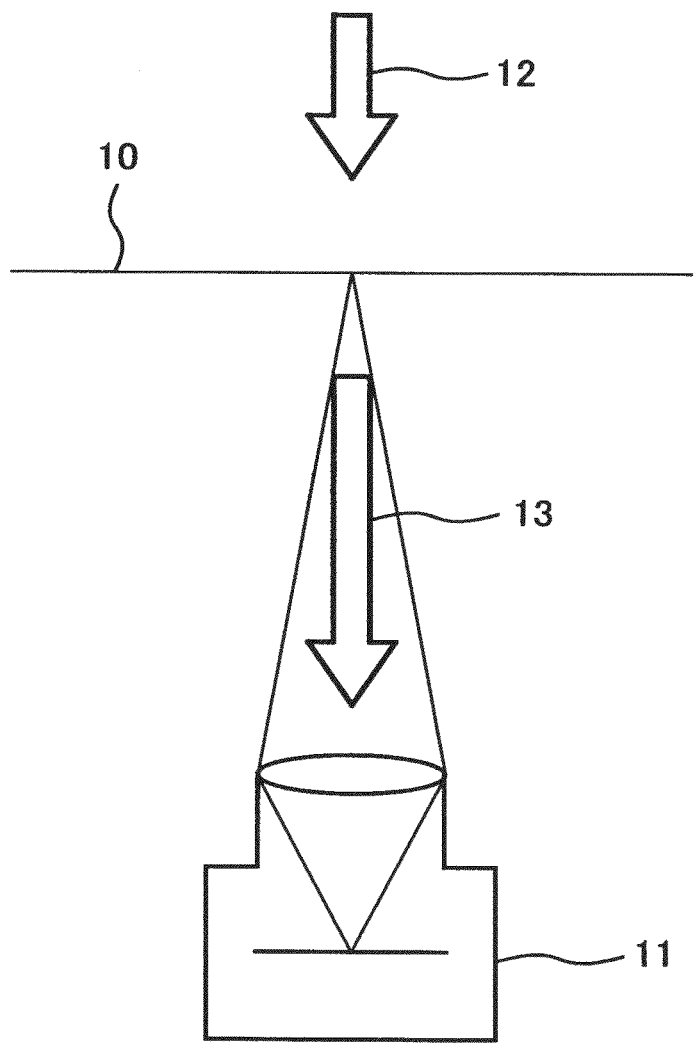
FIG. 1 shows a schematic view illustrating a state of scattering of illuminating rays in a dish absent of pluripotent stem cells.
Figure 2:
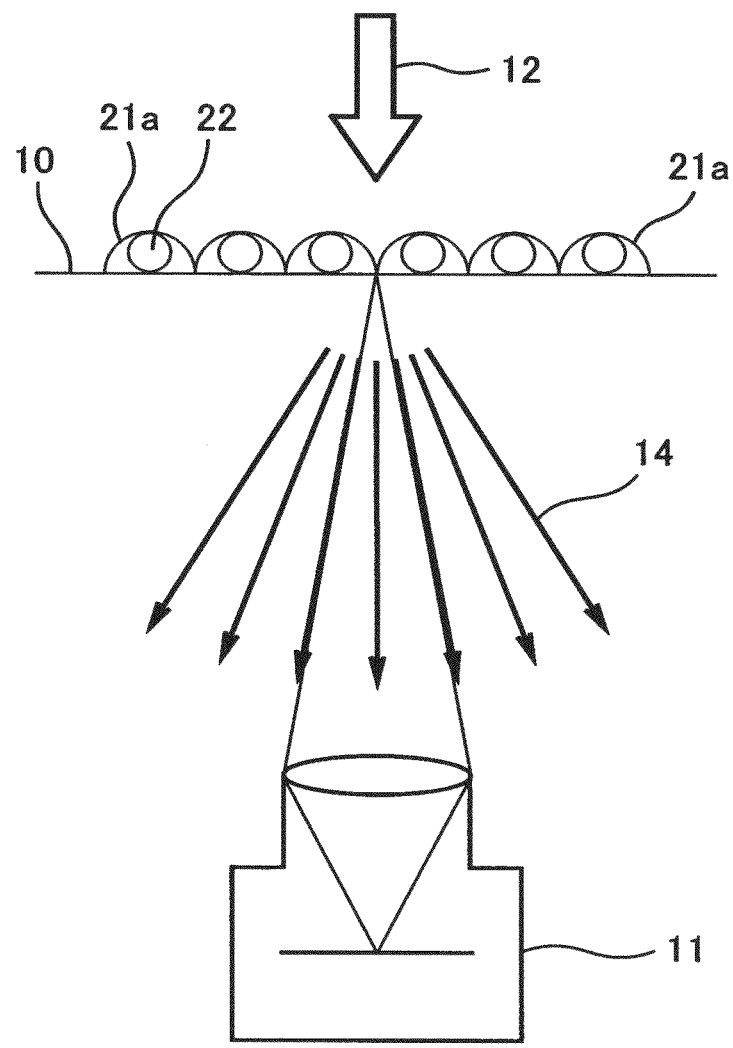
FIG. 2 shows a schematic view illustrating a state of scattering of illuminating rays in a dish including undifferentiated pluripotent stem cells.
Figure 3:
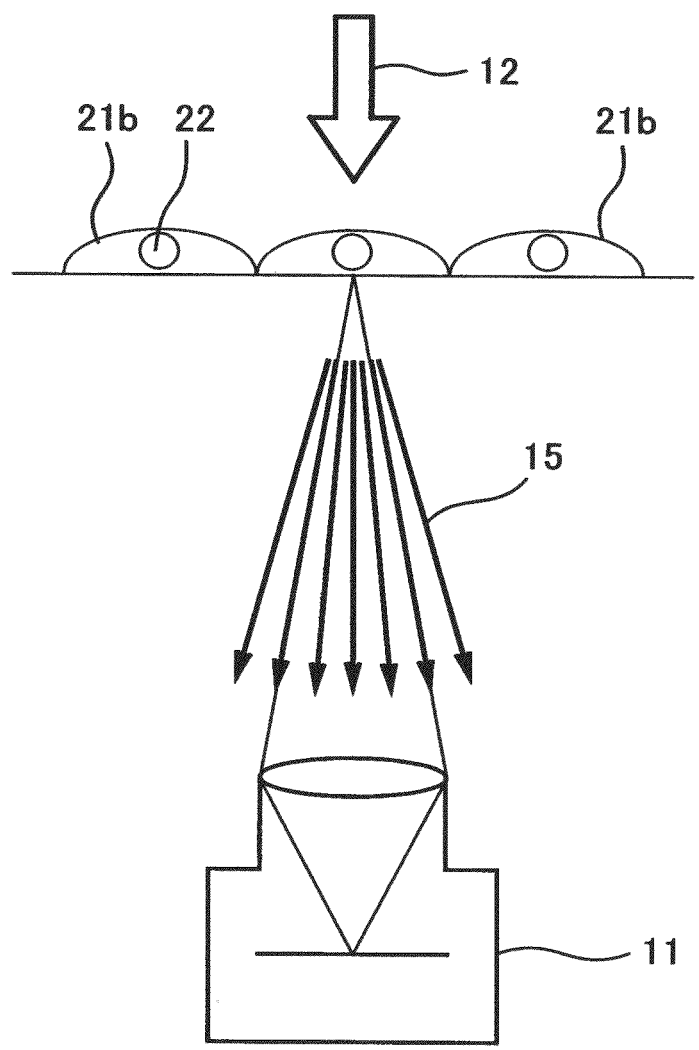
FIG. 3 shows a schematic view illustrating a state of scattering of illuminating rays in a dish including differentiated pluripotent stem cells.
Figure 4:
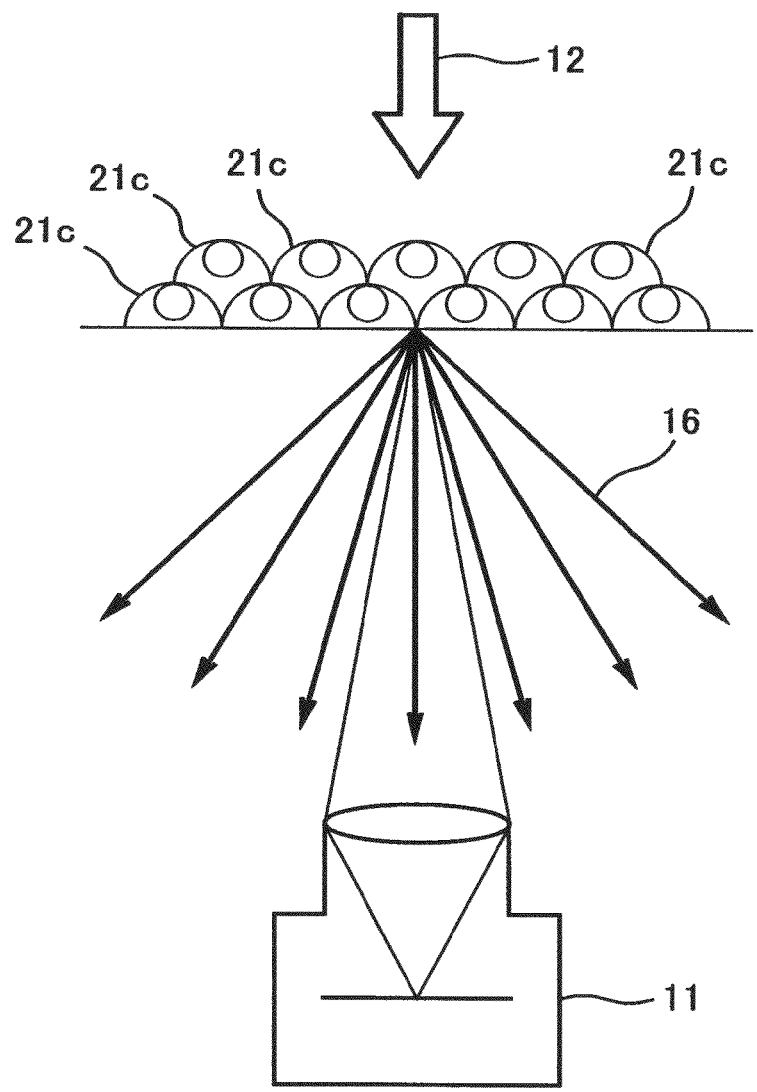
FIG. 4 shows a schematic view illustrating a state of scattering of illuminating rays in a dish including multilayered pluripotent stem cells.

The following findings underlie the colony discrimination based on the luminance. Specifically, in the case in which cells are not adhering to a bottom face 10 of a dish as shown in FIG. 1, illuminating rays 12 penetrate through a bottom face 10 of the dish and then reach as image-carrying rays 13 to an image recording apparatus 11 composed of a camera with almost no scattering. Thus, the resulting image becomes bright. To the contrary, in the case in which pluripotent stem cells are adhering to the bottom face 10 of the dish as shown in FIG. 2, illuminating rays 12 are scattered by pluripotent stem cells 21a. In these regards, as compared with differentiated stem cells described later, undifferentiated pluripotent stem cells 21a have a relatively large core 22 with a proportion of the part excluding the core 22 being smaller in the cell, and thus illuminating rays 12 are scattered at a relatively large degree as shown in FIG. 2. Therefore, a lower level of image-carrying rays 14 reach the image-recording apparatus 11, leading to formation of the resulting image darker at parts corresponding to the undifferentiated pluripotent stem cells 21a. On the other hand, in differentiated pluripotent stem cells, a part excluding a core 22 is larger relative to the core 22 and thus the core 22 is relatively smaller as shown in FIG. 3. Thus, illuminating rays 12 are less scattered as compared with the case of undifferentiated pluripotent stem cells shown in FIG. 2, and a greater level of image-carrying rays 15 reach the image-recording apparatus 11. Therefore, the image at parts corresponding to differentiated pluripotent stem cells 21b of the resulting image becomes brighter compared to the case of the undifferentiated stem cells shown in FIG. 2. Further, in the case of a multilayered colony having pluripotent stem cells 21c stacked in multiple layers resulting from excessive culturing of pluripotent stem cells as shown in FIG. 4, illuminating rays 12 are scattered at greater extent compared to the case of FIG. 2, and thus significantly lower level of image-carrying rays 16 reach an image-recording apparatus 11, thereby leading to formation of the resulting image significantly darker at parts corresponding to the undifferentiated pluripotent stem cells 21c.

In the case of discriminating a colony based on the intensity of the scattered light as described above, the appearance of cells varies depending on an illumination method. Therefore, it is preferred that a transmitted illuminating rays be irradiated from one direction with respect to an observation position so that differentiated cells appear bright, undifferentiated cells appear moderately bright, and cells stacking in multiple layers appear dark.

Figure 5:
FIG. 5 shows a view illustrating a photo image of the interior of a dish.
Figure 6:
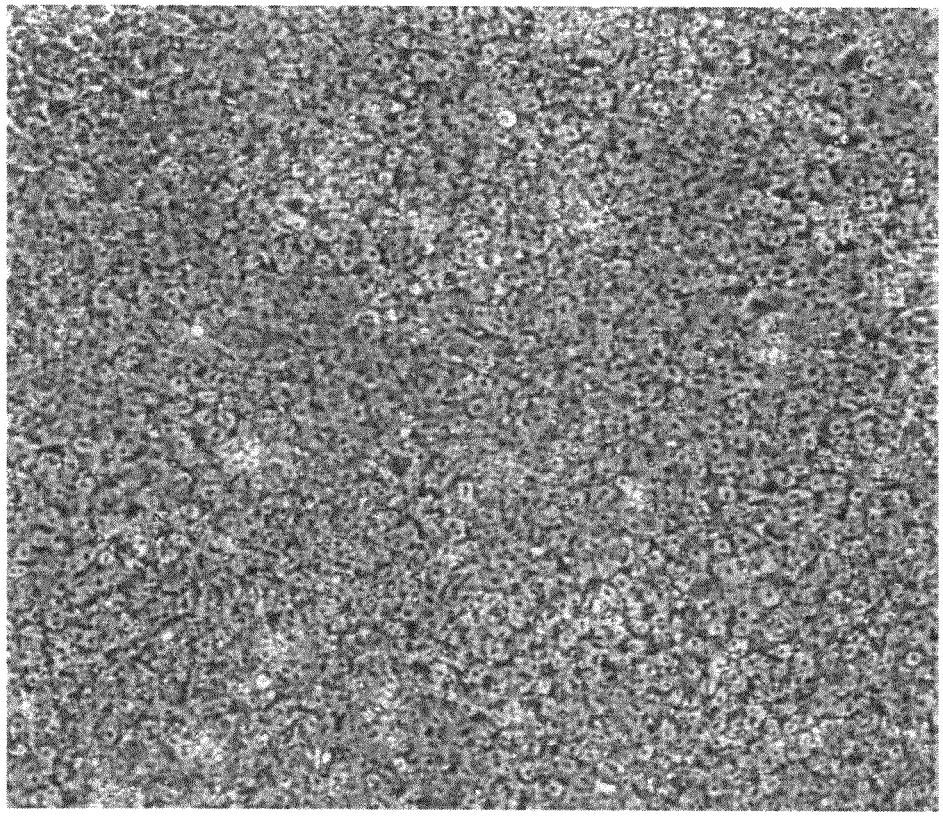
FIG. 6 shows a view illustrating an image of region C of FIG. 5, captured by a phase contrast microscope.
Figure 7:
FIG. 7 shows a view illustrating an image of region D of FIG. 5, captured by a phase contrast microscope.

FIG. 5 shows a photo image of a dish in which iPS cells, a type of pluripotent stem cells, were cultured. FIG. 6 shows an image of a region C of FIG. 5 captured by a phase contrast microscope and subjected to image processing. The region C is an undifferentiated colony composed of undifferentiated pluripotent stem cells. Also, FIG. 7 shows an image of a region D of FIG. 5 captured by a phase contrast microscope and subjected to image processing. In FIG. 7, a region E is composed of differentiated pluripotent stem cells, whereas a region F includes a region in which pluripotent stem cells in multiple layers are present. As can be seen from FIG. 6 and FIG. 7, it is revealed that discrimination among an undifferentiated colony of region C composed of undifferentiated pluripotent stem cells, differentiated pluripotent stem cells of region E and multilayered pluripotent stem cells of a region F is enabled based on the luminance in the photo image. When iPS cells are cultured, there may be cases in which feeder cells are allowed to grow on the entire interior surface of the dish prior to culturing iPS cells to adjust a proliferation environment for iPS cells; however, the feeder cells appear as background noise in the photo image due to the size thereof considerably smaller than iPS cells.

Figure 8:
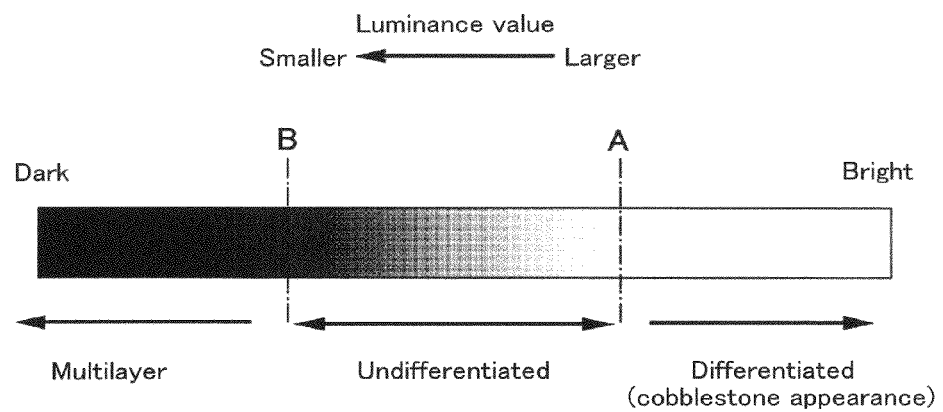
FIG. 8 shows a view illustrating a threshold A and a threshold B used for discriminating among a differentiated colony, an undifferentiated colony and a multilayered colony after image processing.

FIG. 8 schematically shows the criteria for the determination as to which of the three regions described above a particular colony belongs to. In the present invention, as shown in FIG. 8: in case the luminance of the image of a colony is higher than a threshold A, the colony is determined as a differentiated colony; in case the luminance of the image of a colony is equal to or higher than a second threshold B and equal to or lower than a first threshold A, the colony is determined as an undifferentiated region; and a colony having a luminance lower than the second threshold B is determined as a region having multilayered pluripotent stem cells.

Figure 10:
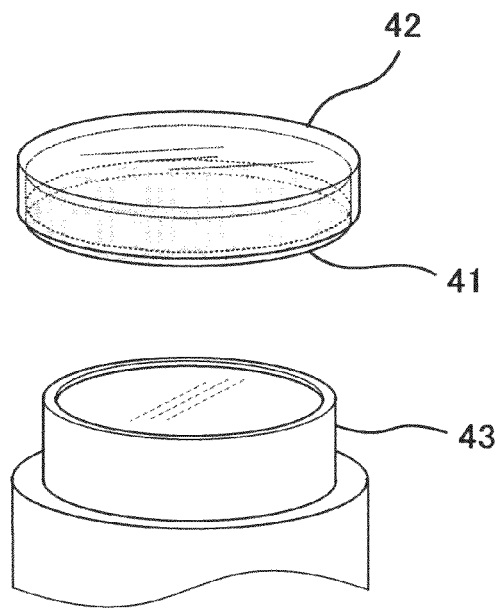
FIG. 10 shows a perspective view illustrating an image-recording apparatus (camera) that takes a photo image of the interior of a dish.
Figure 18:
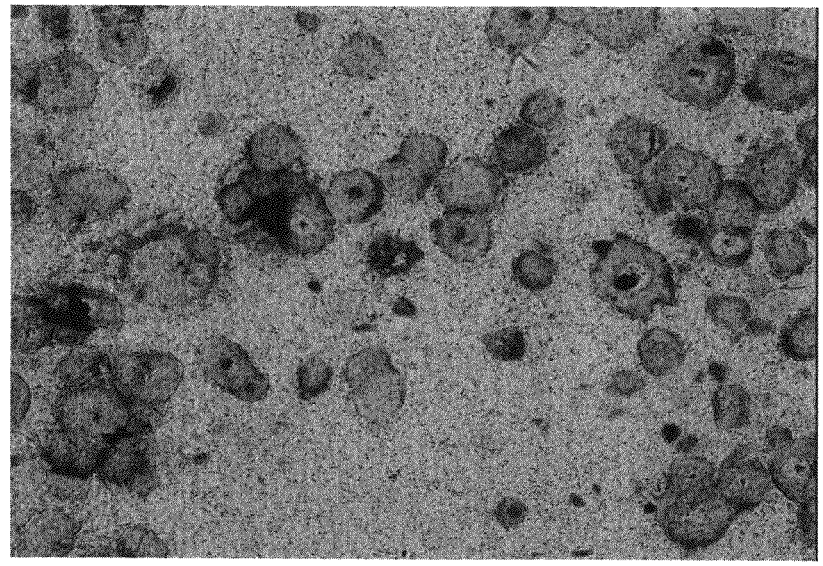
FIG. 18 shows a view illustrating a photo image used for the explanation of a method for determining a first threshold and a second threshold.

Next, a method for determining the first threshold A is explained. First, as shown in FIG. 10, a wide-area photo image of the interior of a dish 41, in which pluripotent stem cells are cultured, is taken by a camera 43 through a cover 42. Then, by normalizing this image to 256 intensity levels, the image shown in FIG. 18 is obtained. Capturing an image of the interior of the dish 41 may be carried out without the cover 42.

Next, a median filtered image is produced by applying median filtering once or multiple times to the image shown in FIG. 18. A median filter is capable of eliminating images of feeder cells and fine noise while maintaining the edge information of the image. In this process, the number of times of the median filtering may be decided depending on the noise level, the actual lead of one pixel on the image, and filter size.

Specific explanation for the determination of the number of times of the median filtering is provided below. In the image of FIG. 18, feeder cells appear as noise. Although the size of common feeder cells is about 300 μm in length and 30 μm in width, there exist feeder cells as large as 100 μm in width. To capture an image of FIG. 18, a camera having an imaging element spacing of 4.6 μm, and a lens with 0.218 times magnification were used. In this case, the actual lead of 1 pixel is 21.3 μm. Herein, a filter which processes within an area of 3×3 pixels is employed and therefore, the filtering of single time uses in, for example, the transverse orientation, information contained in the actual lead equivalent to 2 pixels to execute the processing. The filtering of ten times uses information contained in an actual lead equivalent to 20 pixels to execute the processing. In the case of the filtering to be applied to the noise having a size of 100 μm that is the maximum width of feeder cells, it is effective to conduct the filtering using a range at least the double the size of the noise. In the case of the image shown in FIG. 18, it is preferable to employ a filter that processes a range of 200 μm, which requires the filtering of 5 or more times. In this Embodiment, the number of times of the filtering was set at 10, the double the minimum that is required in order to achieve a more improved filtering effect.

Figure 20:
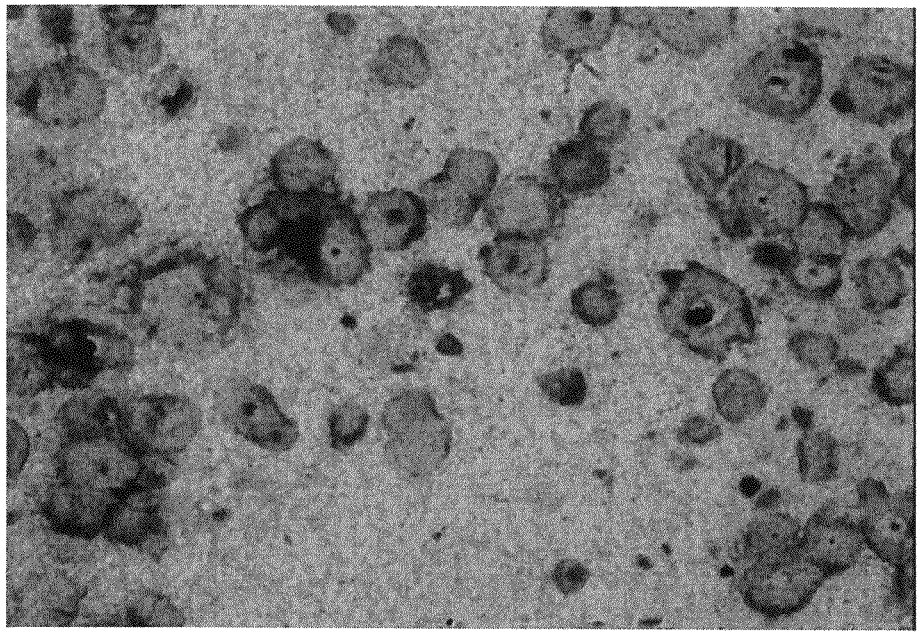
FIG. 20 shows an image resulted from applying median filtering ten times to the image shown in FIG. 18.

FIG. 20 shows an image obtained after subjecting the image shown in FIG. 18 to the median filtering ten times. As is seen from FIG. 20, a small images and noise seemed to be yielded by feeder cells were eliminated in the image after the median filtering. Next, with respect to the median filtered image, a distribution of the number of pixels with respect to the luminance value is obtained. Further, applying a discriminant analysis to this distribution yields a first threshold A. In the present embodiment, a first threshold A was found to be 132.

Figure 19:
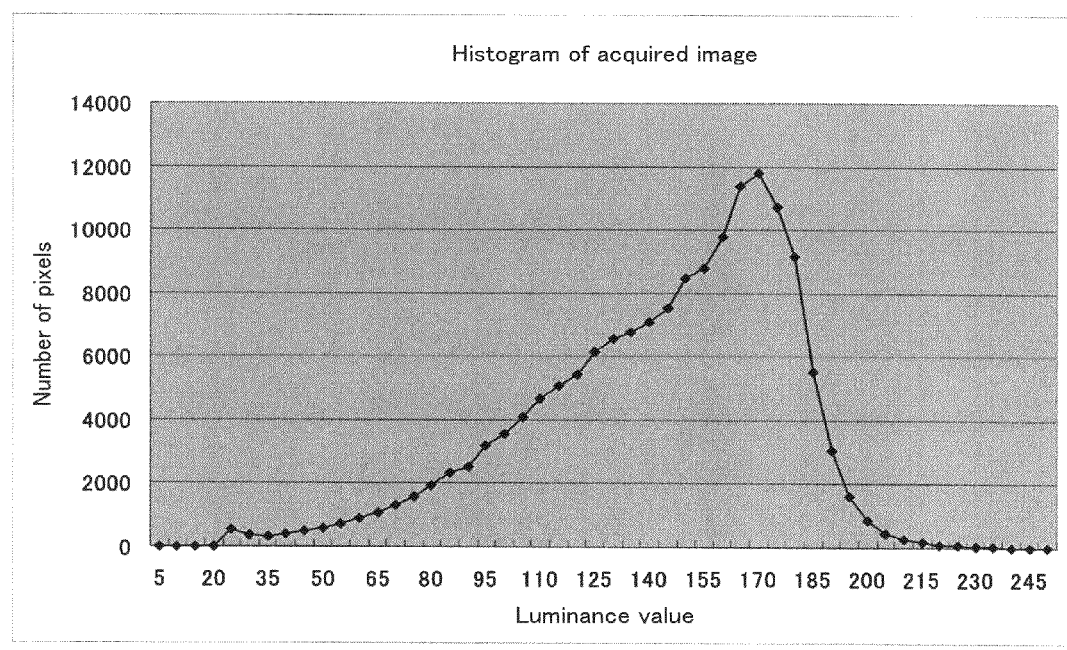
FIG. 19 shows a histogram illustrating the distribution of the number of pixels with respect to the luminance value obtained from the image shown in FIG. 18.
Figure 21:
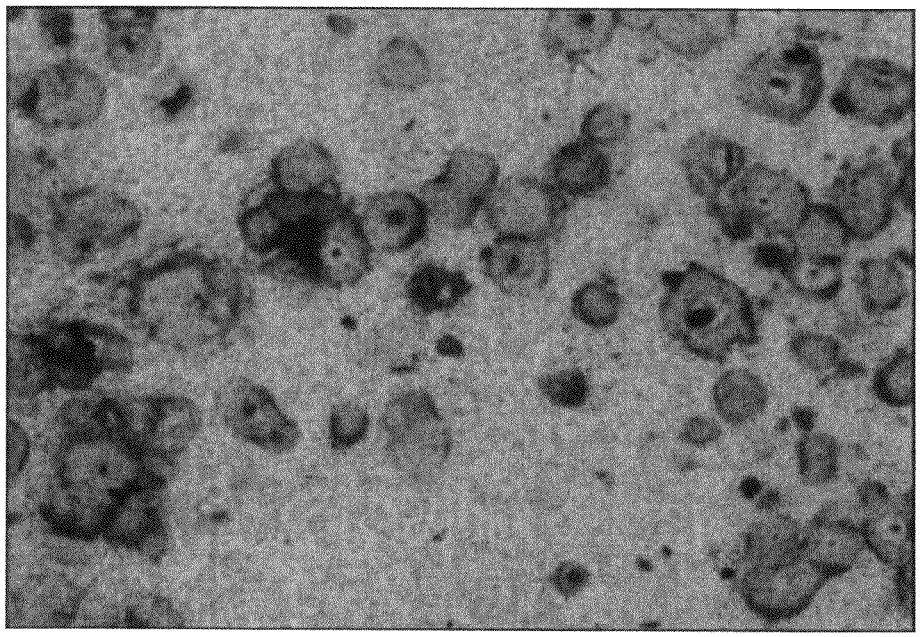
FIG. 21 shows an image resulted from applying Gaussian filtering ten times to the image of FIG. 18.
Figure 22:
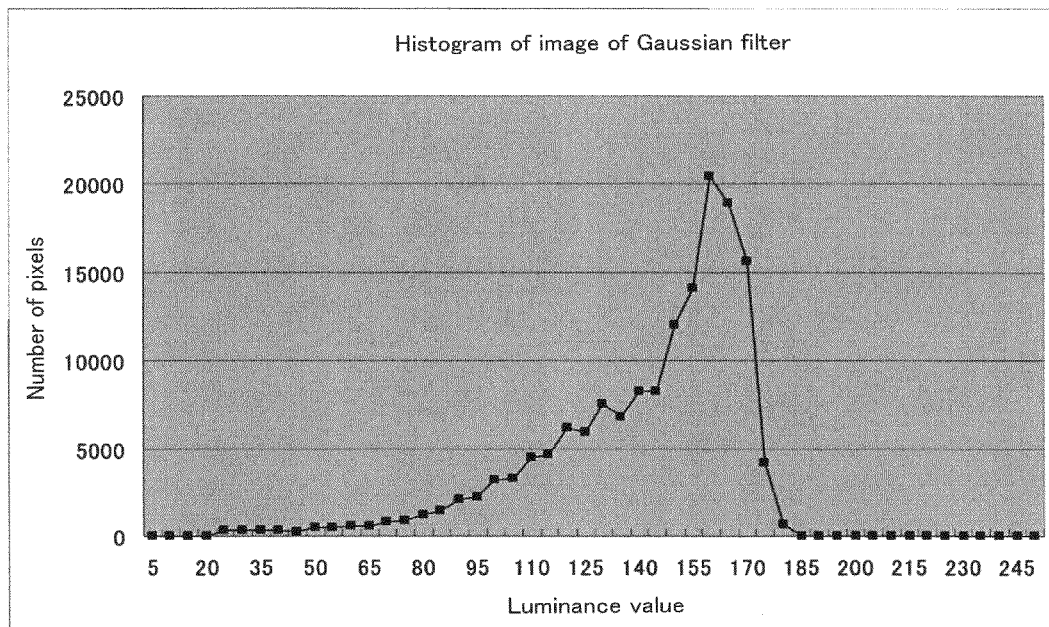
FIG. 22 shows a histogram illustrating the distribution of the number of pixels with respect to the luminance value obtained from the image shown in FIG. 21.

Next, a method for determining the second threshold B is explained. In determining the second threshold B, a colony threshold used for extracting only a region having a colony is first determined. The colony threshold is determined by using a histogram (see FIG. 19) showing the distribution of the number of pixels with respect the luminance value for the image shown in FIG. 18. First, a Gaussian filtered image is produced by applying Gaussian filtering that is a type of a smoothing filter, once or multiple times to the image of FIG. 18. Gaussian filters are capable of eliminating noise and preventing large difference in luminance between a target pixel and its neighboring pixels, thereby enabling a smooth image to be obtained. In this respect, other filter, e.g., a moving average filter may be used as the smoothing filter. The number of times of the Gaussian filtering may be decided depending on the noise level, the actual lead of one pixel on the image, and filter size. The detailed explanation is similar to that in the foregoing case of the number of times of the median filtering. In this embodiment, Gaussian filtering was applied ten times. FIG. 21 shows an image after subjecting the Gaussian filtering ten times, and FIG. 22 shows a histogram of the same. A comparison of FIG. 18 with FIG. 21 shows that the image after subjected to the Gaussian filtering is smoother. Also, a comparison of FIG. 19 with FIG. 22 shows that the histogram after subjected to the Gaussian filtering has a higher peak and also that the position of the peak is shifted.

Next, with respect to an image after subjected to the Gaussian filtering, a colony threshold used for discriminating between a region having a colony and a region having no colony is determined. The colony threshold can be calculated by multiplying the first threshold by a predetermined multiplying factor in the range of from 105% to 115%. An image of a region composed only of a colony can be obtained by extracting pixels with a luminance lower than the colony threshold.

Herein, the multiplying factor applied to the first threshold is determined by experimental trial described below. Specifically, using a tentative colony threshold set by using a tentatively-set multiplying factor, and a tentative colony extraction image is produced. The colony extraction range thus obtained is compared with a colony range determined by a human with visual observation, telescopic observation, or judgment based on a stained image, and in the case in which the colony range set by human inspection is larger, the multiplying factor is increased. In addition, the colony extraction range obtained in this process is compared with a colony range determined by a human with visual observation, telescopic observation, or judgment based on a stained image, and in the case in which the colony range set by human inspection is smaller, the multiplying factor is decreased. Once the image capturing condition, culture condition for pluripotent stem cells and the type of pluripotent stem cell strain to be cultured are decided, the multiplying factor becomes fixed. In this embodiment, the multiplying factor was set at 110% and the luminance value of 145 was set as the colony threshold.

Figure 23:
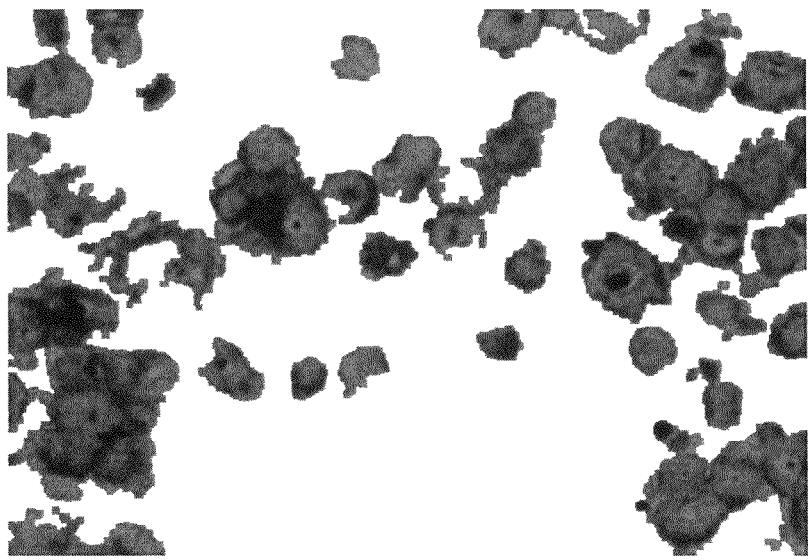
FIG. 23 shows an image of colonies being extracted with the use of a threshold calculated by multiplying a first threshold by a predetermined multiplying factor in the range of from 105% to 115%.
Figure 24:
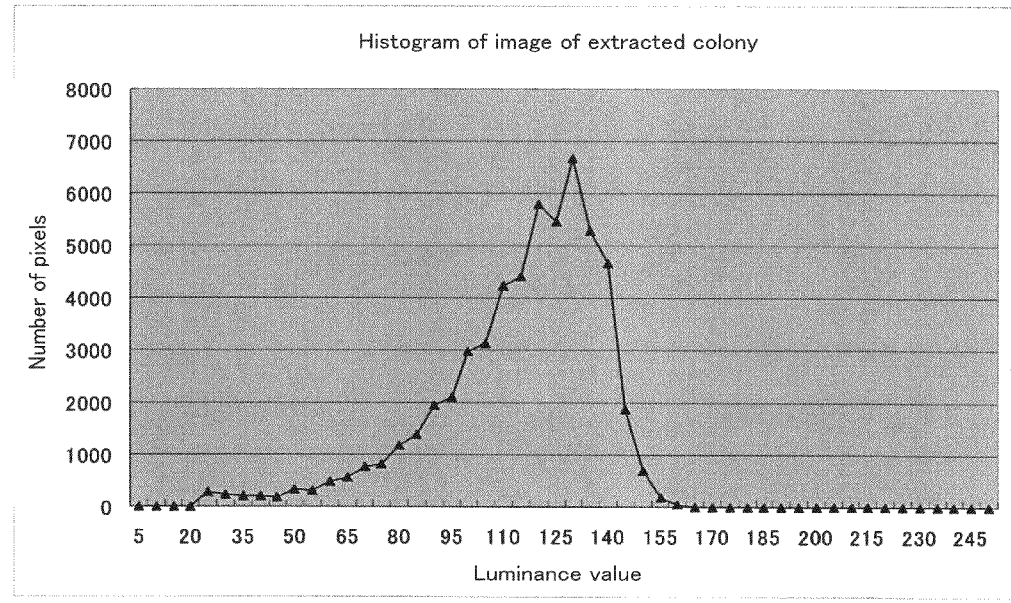
FIG. 24 shows a histogram illustrating the distribution of the number of pixels with respect to the luminance value obtained from the image shown in FIG. 23.

FIG. 23 shows an image of colonies extracted in this manner. Colonies having a small area deemed to be unsuitable for being detached and recovered were excluded. Also in FIG. 23, a region being present inside the colony having a luminance value higher than 145 is also regarded as a part of the colony. FIG. 24 shows a histogram illustrating the distribution of the number of pixels with respect to the luminance value of FIG. 23. Since the area other than the colonies is all white (luminance value: 255) in FIG. 23, the number of pixels corresponding to the luminance value of 255 in FIG. 24 is extremely large (not shown in the figure).

Figure 25:
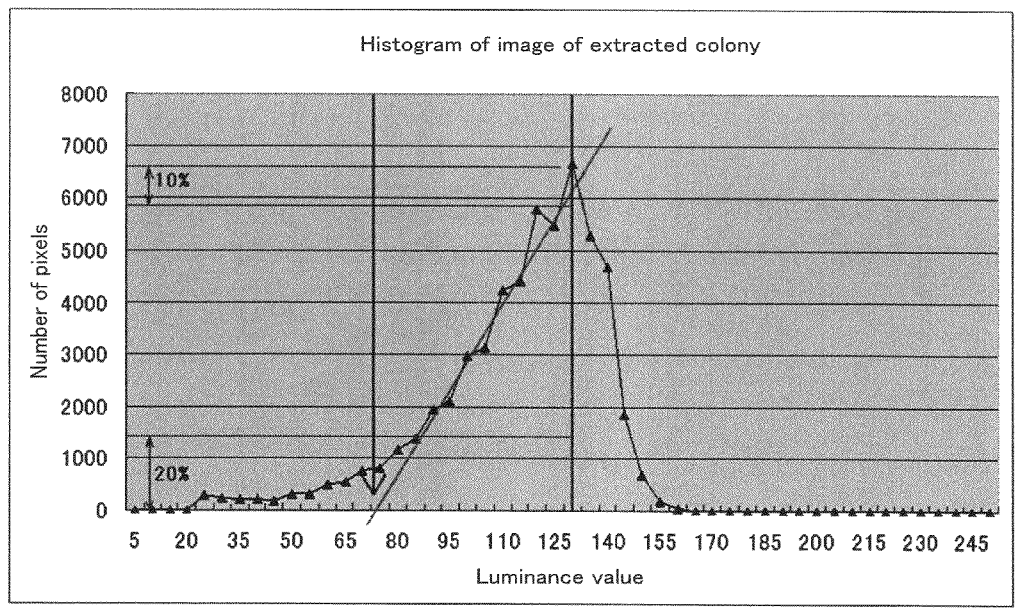
FIG. 25 shows an explanatory view illustrating the method for determining a second threshold by using the histogram shown in FIG. 24.

After the image of the colonies is extracted in such way, the second threshold is determined. In the histogram shown in FIG. 24, the smaller value of: the first threshold A of 132; and the luminance value corresponding to the maximum value of the histogram, namely the luminance value of 130, is set as the maximum luminance limit which determines the calculation range used in the least squares method as in the following. In the present embodiment, the maximum luminance limit was 130. As shown in FIG. 25, a straight line is obtained by the least squares method using the coordinates of the points on the histogram that lie between 20% and 90% of the number of pixels (the value of vertical coordinate) corresponding to the maximum luminance limit. Next, the intersection point between the straight line obtained by the least squares method and the horizontal axis is determined as the second threshold B. In the present embodiment, the second threshold was 73.

Figure 26:
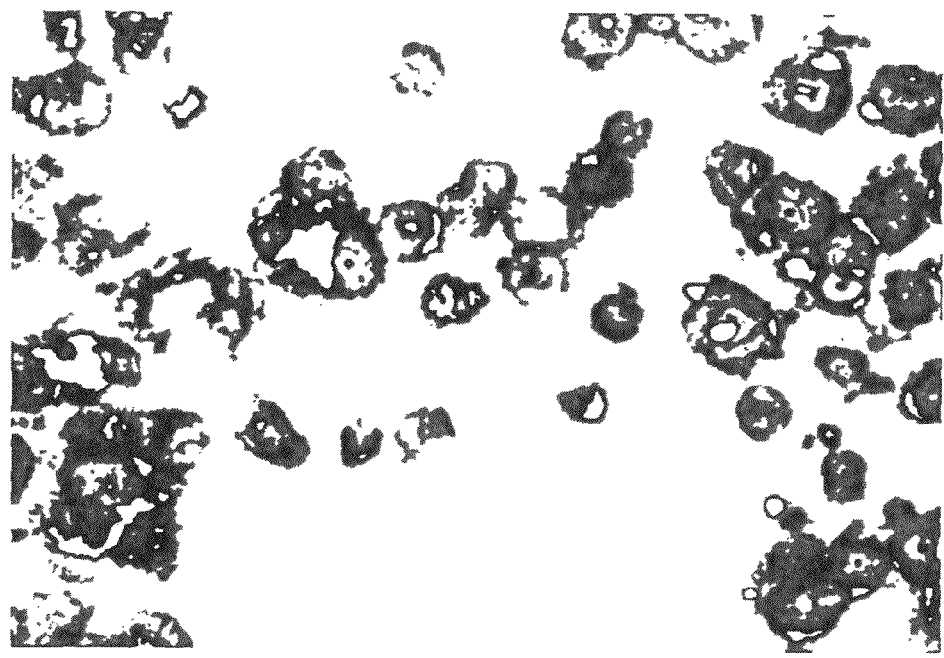
FIG. 26 shows an image composed only of the regions having a luminance being equal to or lower than the first threshold of 132 and being equal to or higher than the second threshold of 73 shown in the image of FIG. 18.

The image of only undifferentiated cells can be obtained by the second threshold B determined as in the foregoing and the first threshold A described above. Specifically, the image composed only of a region with a luminance equal to or lower than the first threshold of 132 and equal to or higher than the second threshold of 73 was determined as an image of only undifferentiated cells. FIG. 26 shows an image of only undifferentiated cells obtained as above in the present embodiment.

In the case in which cells that are in fact undifferentiated are determined as differentiated cells when as the first threshold A the luminance value of 132 derived according to the discriminant analysis as described in the foregoing was used, more accurate discrimination of undifferentiated cells may be enabled by using as the first threshold A the luminance value calculated by multiplying the threshold derived according to the discriminant analysis by a predetermined multiplying factor in the range of from 100% to 115% (but not exceeding the multiplying factor used for obtaining the colony threshold). In this respect, the multiplying factor to be applied to the threshold derived according to the discriminant analysis is determined by experimental trials.

Using a tentative first threshold set with a multiplying factor of 100%, an image of only undifferentiated colonies is obtained. With respect to the image of only the undifferentiated colonies obtained, as long as a large number of undifferentiated colony regions with a minute area are present, the multiplying factor is increased, and when the multiplying factor results in almost null undifferentiated colony regions with a minute area, such a multiplying factor is determined as the multiplying factor to be applied to the aforementioned threshold derived according to the discriminant analysis. The threshold calculated by using this multiplying factor is determined as the first threshold. Once the image capturing condition, culture condition for pluripotent stem cells and the type of pluripotent stem cell strain to be cultured are decided, the multiplying factor becomes fixed.

In FIG. 26, since a large number of undifferentiated colony regions with a minute area are present, it is preferable to increase the multiplying factor.

Figure 27:
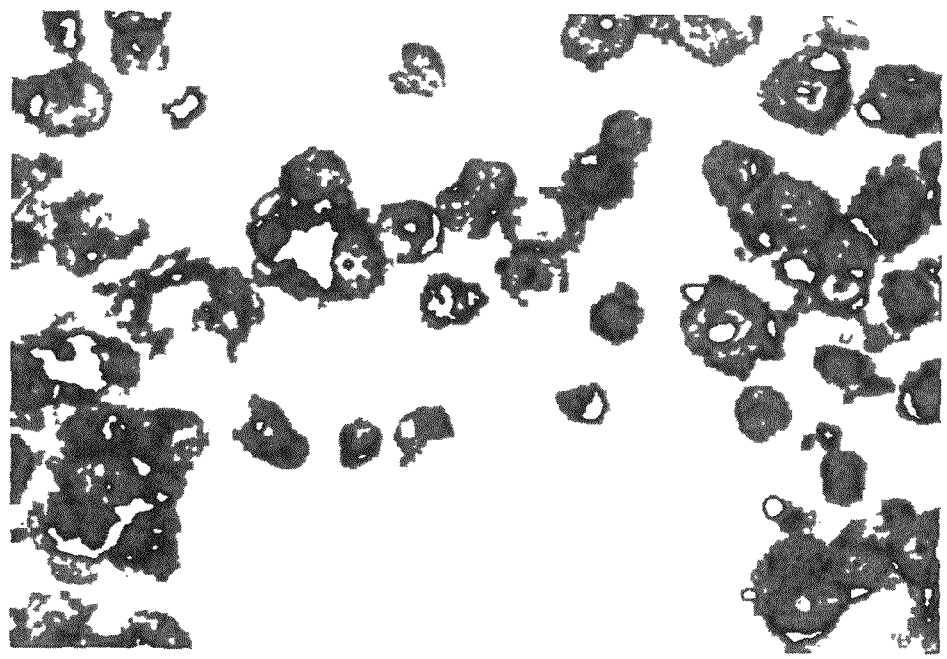
FIG. 27 shows an image composed only of the regions having a luminance being equal to or lower than the first threshold of 140 and being equal to or higher than the second threshold of 73 shown in the image of FIG. 18.

FIG. 27 shows an image of only undifferentiated cells obtained with the first threshold of 140. This demonstrates the casein which the multiplying factor employed was 106%. As can be seen in FIG. 27, since a very small number of undifferentiated colony regions with a minute are present, it is preferable to use the first threshold A of 140.

Figure 9:
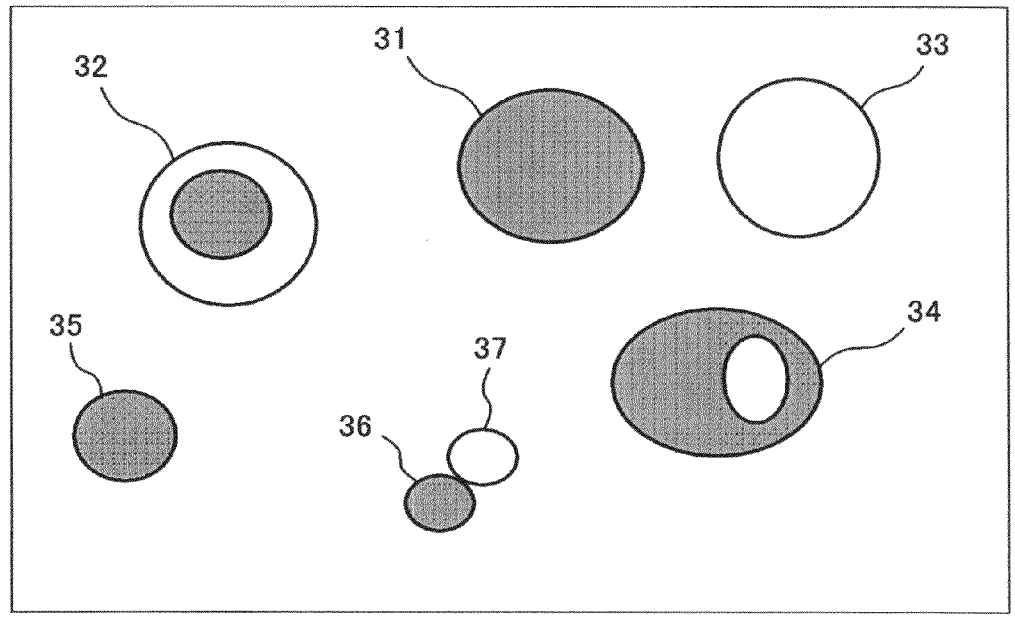
FIG. 9 shows a schematic view of an interior of a culture vessel containing a mixture of a differentiated colony containing differentiated pluripotent stem cells, and an undifferentiated colony containing only undifferentiated pluripotent stem cells.

Thereafter, undifferentiated pluripotent stem cells are recovered from the colony as follows. FIG. 9 schematically shows a photo image of a culture vessel containing a mixture of undifferentiated colonies and differentiated colonies, with undifferentiated region being shown as a dark shade area and differentiated region by an enclosed white area. First, independent colonies 31 and 35 containing only undifferentiated pluripotent stem cells are selected as a colony to be detached and recovered. A colony 32 with the circumference having started to differentiate is excluded from the colony to be detached. An entirely differentiated colony 33 is also excluded. Further, a colony 34 with partially differentiated interior is also excluded from the colony to be detached. Although a colony 36 is composed only of undifferentiated pluripotent stem cells, the colony 36 is not selected since detachment thereof with a solution discharged from a pipetting unit as described later results in detachment of differentiated pluripotent stem cells from a differentiated colony 37 existing adjacent to the colony 36, and thus can be affected by the pipetting liquid flow. In such selection of colonies, it is necessary to take into consideration alterations of the physically effected area, depending on a type of tip attached to the pipetting unit and the discharge speed of a discharged solution. It is possible to detach only undifferentiated colonies even in the case in which the distance between the undifferentiated colony and the differentiated colony is small, by using for the detaching a cloning ring or a glass capillary that has higher positional precision than the pipetting unit.

Figure 11:
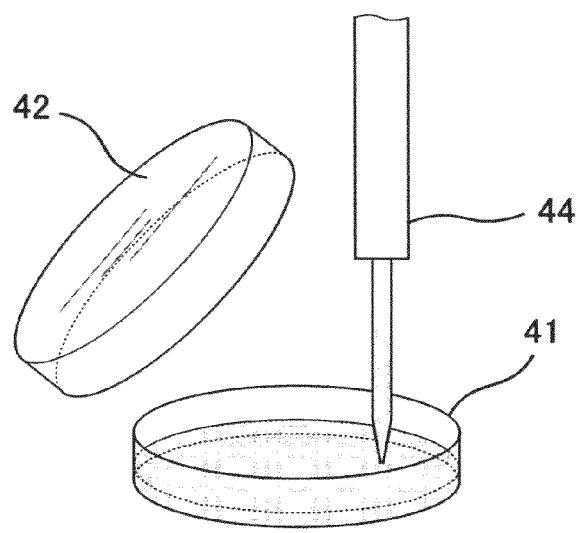
FIG. 11 shows a perspective view illustrating a pipetting unit for detaching an undifferentiated colony by discharging a culture fluid by pipetting.
Figure 12:
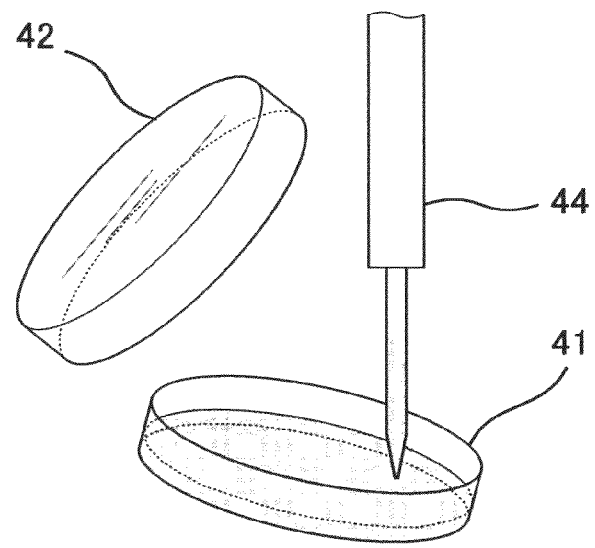
FIG. 12 shows a perspective view illustrating a pipetting unit for recovering undifferentiated pluripotent stem cells detached by pipetting.

Next, after selecting undifferentiated colonies from which pluripotent stem cells are to be recovered, the recovery of pluripotent stem cells is carried out with the pipetting unit. First, a cell detaching agent is introduced into the entire culture vessel. The type, concentration and quantity of the cell detaching agent are determined so that cells adhering to the bottom face of the dish can be detached during a predetermined detachment period by the liquid flow of a culture fluid resulting from a discharging operation with the pipetting unit, and that cells are left undetached from the bottom face in the absence of a liquid flow. After a detaching solution containing the cell detaching agent is introduced, a culture medium is discharged from pipetting unit 44 towards a selected undifferentiated colony as shown in FIG. 11 and the resulting liquid flow detaches only the undifferentiated pluripotent stem cells. The number of times of the discharge of the culture medium from the pipetting unit is not limited to once, and thus multiple discharges may be carried out from the same position or from varying positions. The discharge speed and solution quantity may be also changed. After completing the detachment of the undifferentiated colonies which should be detached, the solution containing the undifferentiated pluripotent stem cells is recovered with the pipetting unit 44 by tilting dish 41 as necessary as shown in FIG. 12 and when subculturing is further required, the solution is dispensed into a dish 41 containing a fresh culture medium.

Figure 13:
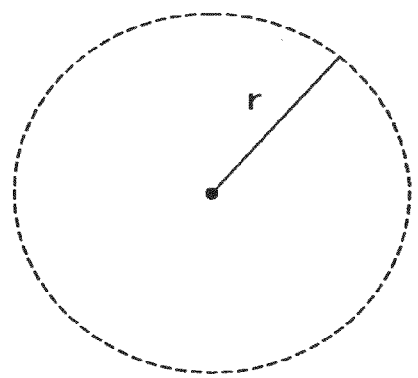
FIG. 13 shows a schematic view illustrating an area detached by one operation of pipetting.
Figure 14:
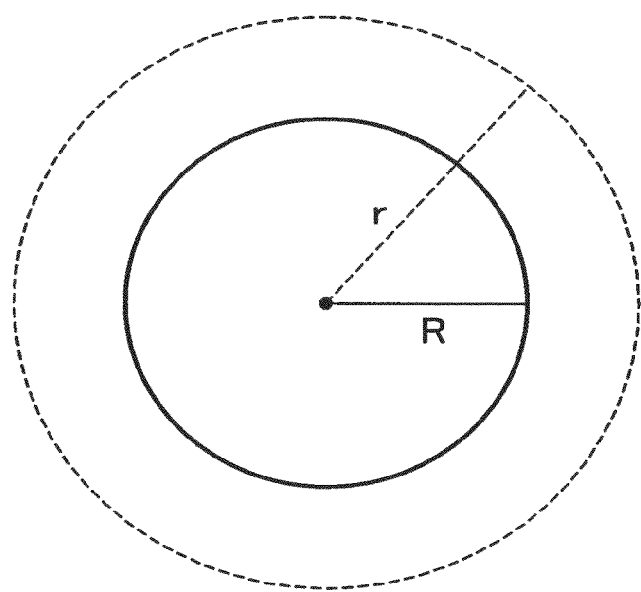
FIG. 14 shows a schematic view illustrating a pipetting operation in the case in which the size of an undifferentiated colony is smaller than the area that can be detached by one operation of pipetting.
Figure 15:
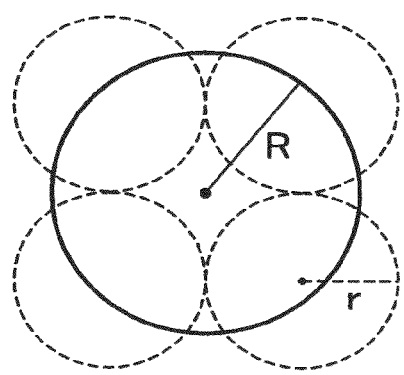
FIG. 15 shows a schematic view illustrating a pipetting area in the case in which the size of an undifferentiated colony is larger than the area that can be detached by one operation of pipetting.
Figure 16:
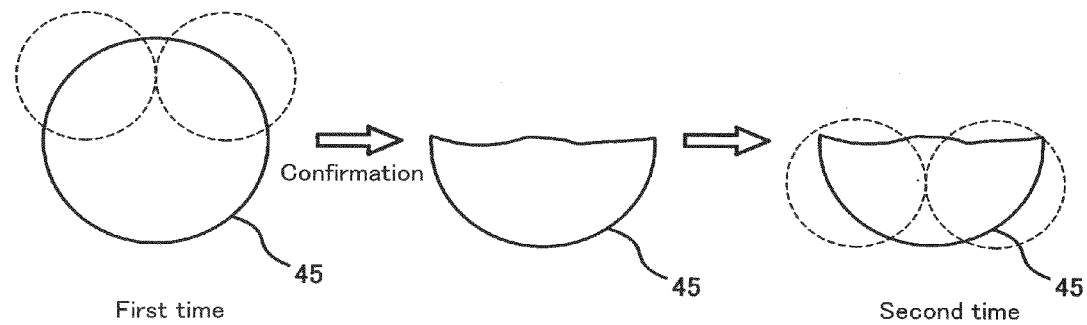
FIG. 16 shows a schematic view illustrating a procedure of pipetting operations in the case in which the size of an undifferentiated colony is larger than the area that can be detached by one operation of pipetting.
Figure 17:
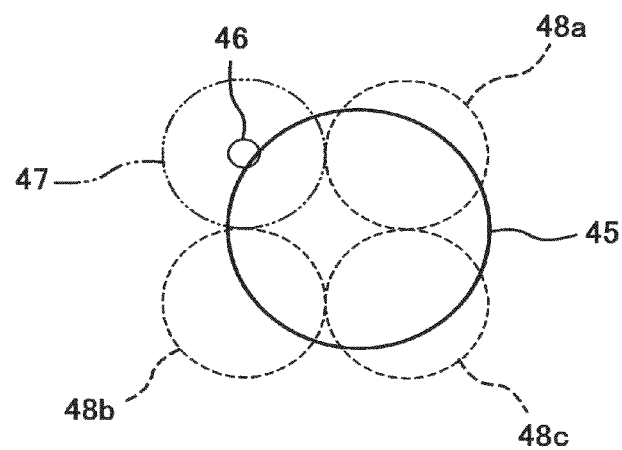
FIG. 17 shows a schematic view illustrating pipetting operations in the case in which a differentiated colony is present in the vicinity of an undifferentiated colony.

The following explains pipetting carried out for detaching an undifferentiated colony. The diameter of the area in which the cells are detached by pipetting is defined as r as shown in FIG. 13. In the case in which a completely independent colony is to be detached, free from adjacent other colony such as a differentiated colony which should not be detached, the entire colony can be detached by one operation of the pipetting as long as a diameter r of the area that can be detached by pipetting is larger than a diameter R of the colony to be detached. Alternatively, when a diameter r of the area that can be detached by one operation of the pipetting is smaller than a diameter R of the colony to be detached, the entirety of the undifferentiated colony is detached by multiple operations of the pipetting as shown in FIG. 15 (four operations in the case of FIG. 15). The procedure in such a case involves as shown in FIG. 16, first detaching the upper portion of an undifferentiated colony 45 by two operations of the pipetting and after the confirmation of the state of detachment, the lower portion of the undifferentiated colony 45 is detached by additional two operations of the pipetting, thereby completing the detachment of the entire colony. On the other hand, in the case in which the differentiated colony 46 exists in the vicinity of the undifferentiated colony 45 as shown in FIG. 17, a detaching operation by pipetting is not carried out for a region 47 including the differentiated colony 46, and only the three regions, 48a, 48b and 48c are detached by pipetting.

While the case in which only undifferentiated colonies are detached and recovered is explained above, it is possible to configure that after all of colonies other than undifferentiated colonies be detached and discarded by using the pipetting unit 44, all of undifferentiated colonies left in the dish may be detached and recovered at once. Alternatively, different pipetting units may be used for recovering undifferentiated colonies and for discarding colonies other than undifferentiated colonies, respectively.

Further, in the present invention, it is possible to configure such that after acquiring the positional information of each colony from a wide-area photo image, the magnified image (phase difference equivalent image) of a colony is captured based on the positional information, and a human confirms and estimates the magnified image. It is also possible to automatically select a colony more accurately based on the magnified image.

INDUSTRIAL APPLICABILITY

According to the colony discrimination method and apparatus, and automated culture method and system of undifferentiated stem cells of the present invention, only undifferentiated stem cells can be selectively subcultured, and therefore suitable for application in the field of regenerative medicine.

REFERENCE SIGNS LIST

10: bottom face of dish
11: image recording apparatus
12: illuminating ray
13, 14, 15, 16: image-carrying ray
21a: undifferentiated pluripotent stem cells
21b: differentiated pluripotent stem cell
21c: multilayered pluripotent stem cell
22: core
41: dish
42: cover
43: camera
31: undifferentiated colony
32, 33, 34: differentiated colony
35, 36: undifferentiated colony
37: differentiated colony
44: pipetting unit
45: undifferentiated colony
46: differentiated colony
47: detached region
48a, 48b, 48c: detached region

The invention claimed is:

1. A method for discriminating a colony based on a photo image of the colony composed of pluripotent stem cells, the method comprising
    discriminating between a differentiated colony containing differentiated pluripotent stem cells and an undifferentiated colony containing only undifferentiated pluripotent stem cells based on the luminance of the photo image,
wherein
    a colony having a region with a luminance higher than the first threshold of the luminance is determined as the differentiated colony, and a colony having only a region with a luminance equal to or lower than the first threshold is determined as the undifferentiated colony, and
    the first threshold is determined by applying a discriminant analysis to the distribution of the number of pixels with respect to each luminance value in a median filtered image obtained by applying median filtering once or multiple times to the photo image.

2. The method for discriminating a colony according to claim 1, further comprising discriminating a multilayered colony containing pluripotent stem cells stacked in multiple layers.

3. The method for discriminating a colony according to claim 2, wherein: a colony having a region with a luminance higher than the first threshold of the luminance is determined as the differentiated colony; a colony having only a region with a luminance equal to or lower than the first threshold and equal to or higher than a second threshold is determined as the undifferentiated colony; and a colony having a region with a luminance lower than the second threshold as the multilayered colony.

4. The method for discriminating a colony according to claim 3, wherein
    the first threshold is determined by applying a discriminant analysis to the distribution of the number of pixels with respect to each luminance value determined on a median filtered image obtained by applying median filtering once or multiple times to the photo image; and
    the second threshold is determined by: obtaining an image of only the colony region by extracting, out of the pixels in the smoothing filtered image obtained by applying smoothing filtering once or multiple times to the photo image, only the pixels having a luminance value smaller than the threshold calculated by multiplying the first threshold by a predetermined multiplying factor in the range of from 105% to 115%; creating a histogram with respect to each pixel in the image of only the colony region, with the luminance value on the horizontal axis and the number of pixels having the corresponding luminance value on the vertical axis; provided that a maximum luminance limit defined as whichever the smaller luminance value between the first threshold and the luminance value corresponding to the maximum value of the histogram, obtaining within the range of luminance value smaller than the maximum luminance limit, a straight line by the least squares method using the coordinates of the points on the histogram that lie between 20% of the number of pixels corresponding to the maximum luminance limit and 90% of the number of pixels corresponding to the maximum luminance limit; and obtaining the intersection point of the straight line and the horizontal axis to give the second threshold.

5. A method for automatically culturing undifferentiated pluripotent stem cells, the method comprising:
discriminating an undifferentiated colony from a colony other than the undifferentiated colony by the method for discriminating a colony according to claim 1; acquiring the positional information of the undifferentiated colony and that of the colony other than the undifferentiated colony;
introducing a cell detaching agent into the culture vessel;
detaching the undifferentiated colony based on the positional information; and
recovering the undifferentiated pluripotent stem cells obtained by detaching the undifferentiated colony.

6. A method for automatically culturing undifferentiated pluripotent stem cells, the method comprising:
discriminating an undifferentiated colony from a colony other than the undifferentiated colony by the method for discriminating a colony according to claim 1;
acquiring the positional information of the undifferentiated colony and that of the colony other than the undifferentiated colony;
introducing a cell detaching agent into the culture vessel;
detaching the colony other than the undifferentiated colony based on the positional information;
discarding the pluripotent stem cells obtained by detaching the colony other than the undifferentiated colony; and
recovering the undifferentiated pluripotent stem cells by detaching the undifferentiated colony.

7. A colony discrimination apparatus, comprising
an image input unit for inputting a photo image after subjected to image processing based on the luminance value, and
a discrimination unit for discriminating between a differentiated colony containing differentiated pluripotent stem cells and an undifferentiated colony composed only of undifferentiated pluripotent stem cells,
the discrimination unit determines a colony having a region with a luminance higher than the first threshold of the luminance as the differentiated colony; and a colony having only a region with a luminance equal to or lower than the first threshold as the undifferentiated colony; and
the first threshold is determined by applying a discriminant analysis to the distribution of the number of pixels with respect to each luminance value determined on a median filtered image obtained by applying median filtering once or multiple times to the photo image.

8. The colony discrimination apparatus according to claim 7, wherein the discrimination unit further discriminates a multilayered colony containing pluripotent stem cells stacked in multiple layers based on the luminance of the colony.

9. The colony discrimination apparatus according to claim 7, wherein the discrimination unit determines: a colony having a region with a luminance higher than the first threshold as the differentiated colony; a colony having only a region with a luminance equal to or lower than the first threshold and equal to or higher than a second threshold as the undifferentiated colony; and a colony having a region with a luminance lower than the second threshold as the multilayered colony.

10. The colony discrimination apparatus according to claim 9, wherein
the first threshold is determined by applying a discriminant analysis to the distribution of the number of pixels with respect to each luminance value determined on a median filtered image obtained by applying median filtering once or multiple times to the photo image; and
the second threshold is determined by: obtaining an image of only the colony region by extracting, out of the pixels in the smoothing filtered image obtained by applying smoothing filtering once or multiple times to the photo image, only the pixels having a luminance value smaller than the threshold calculated by multiplying the first threshold by a predetermined multiplying factor in the range of from 105% to 115%; creating a histogram with respect to each pixel in the image of only the colony region, with the luminance value on the horizontal axis and the number of pixels having the corresponding luminance value on the vertical axis; provided that a maximum luminance limit defined as whichever the smaller luminance value between the first threshold and the luminance value corresponding to the maximum value of the histogram, obtaining within the range of luminance value smaller than the maximum luminance limit, a straight line by the least squares method using the coordinates of the points on the histogram that lie between 20% of the number of pixels corresponding to the maximum luminance limit and 90% of the number of pixels corresponding to the maximum luminance limit; and obtaining the intersection point of the straight line and the horizontal axis to give the second threshold.

11. A system for automatically culturing undifferentiated stem cells, comprising:
the colony discrimination apparatus according to claim 7;
a detaching agent introduction unit for introducing a cell detaching agent into the culture vessel; and
a pipetting unit for detaching the undifferentiated colony based on the positional information of each of the colony and recovering the undifferentiated pluripotent stem cells obtained by detaching the undifferentiated colony.

12. A system for automatically culturing undifferentiated stem cells, comprising:
the colony discrimination apparatus according to claim 7;
a positional information acquisition unit for acquiring the positional information of the undifferentiated colony and that of the colony other than the undifferentiated colony;
a detaching agent introduction unit for introducing a cell detaching agent into the culture vessel; and
a pipetting unit for detaching the colony other than the undifferentiated colony based on the positional information acquired by the positional information acquisition unit, discarding the pluripotent stem cells obtained by detaching the colony other than the undifferentiated colony, and recovering undifferentiated pluripotent stem cells by further detaching the undifferentiated colony.

* * * * *